United States Patent
Poore et al.

Patent Number: 5,423,867
Date of Patent: Jun. 13, 1995

[54] RATE-RESPONSIVE PACEMAKER HAVING AUTOMATIC SENSOR THRESHOLD WITH PROGRAMMABLE OFFSET

[75] Inventors: John W. Poore, South Pasadena; Brian M. Mann, Beverly Hills; Roy B. Medlin, West Hills, all of Calif.

[73] Assignee: Pacesetter, Inc., Sylmar, Calif.

[21] Appl. No.: 844,807

[22] Filed: Mar. 2, 1992

[51] Int. Cl.$^6$ .............................................. A61N 1/362
[52] U.S. Cl. ..................................................... 607/17
[58] Field of Search ......... 128/419 PG; 607/9, 17-26, 607/28

[56] References Cited

U.S. PATENT DOCUMENTS

| | | | |
|---|---|---|---|
| 3,757,792 | 9/1973 | Mulier et al. | 128/419 P |
| 3,949,758 | 4/1976 | Jirak | 128/419 PG |
| 4,240,442 | 12/1980 | Andresen et al. | 128/708 |
| 4,809,697 | 3/1989 | Causey, III et al. | 128/419 PT |
| 4,884,576 | 12/1989 | Alt | 128/419 PG |
| 4,940,052 | 7/1990 | Mann et al. | 128/419 PG |
| 4,940,053 | 7/1990 | Mann et al. | 128/419 PG |
| 4,972,834 | 11/1990 | Begemann et al. | 128/419 PG |
| 5,010,887 | 4/1991 | Thornander | 128/696 |
| 5,040,534 | 8/1991 | Mann et al. | 128/419 PG |
| 5,040,535 | 8/1991 | Mann et al. | 128/419 PG |
| 5,074,302 | 12/1991 | Poore et al. | 128/419 PG |
| 5,101,824 | 4/1992 | Lekholm | 128/419 PG |
| 5,154,170 | 10/1992 | Bennett et al. | 128/419 PG |

Primary Examiner—Lee S. Cohen
Assistant Examiner—Marianne Parker
Attorney, Agent, or Firm—Leslie S. Miller; Lisa P. Weinberg

[57] ABSTRACT

A programmable offset is added to an automatically generated baseline reference value to provide a Threshold value used by the rate-responsive sensor processing circuits of an implantable rate-responsive pacemaker to determine the significance of a sensor input signal. The rate-responsive pacemaker provides stimulation pulses on demand at a pacing rate determined by a sensed physiological parameter. The physiological parameter is sensed by a physiological sensor included within, or coupled to, the rate-responsive pacemaker. The physiological sensor generates a sensor input signal having a magnitude that varies as a function of the sensed physiological parameter. The invention provides a way for the rate-responsive pacemaker, when operating in an autothreshold mode, to automatically determine when the magnitude of the sensor input signal is sufficiently large to justify an increase in the pacing rate. A long-term running average of the sensor input signal is continuously maintained, and is used as a baseline threshold value. A programmable offset is added to the baseline reference value. Any sensor input signal that exceeds the baseline reference value plus the programmable offset is considered to be sufficiently large to effect an increase in the pacing rate.

18 Claims, 4 Drawing Sheets

RATE-RESPONSIVE PACEMAKER HAVING AUTOMATIC SENSOR THRESHOLD WITH PROGRAMMABLE OFFSET

BACKGROUND OF THE INVENTION

1. Field of the Invention

The present invention relates to implantable medical devices and methods, and more particularly to a rate-responsive pacemaker having an automatic sensor threshold with a programmable offset.

In Applicants' earlier U.S. Pat. No. 4,940,052, there is disclosed a microprocessor-controlled, rate-responsive pacemaker having automatic rate response threshold adjustment. The present invention relates to an improvement over the invention disclosed in the '052 patent. The '052 patent is incorporated herein by reference.

As taught in the '052 patent, the rate-responsive pacemaker therein disclosed includes a physiological sensor that generates a raw signal, or "raw sensor signal," as a function of a sensed physiological parameter, which physiological parameter provides an indication of what the pacing rate of the pacemaker should be. The raw sensor signal is converted to one of a plurality of discrete sensor level index signals. The particular sensor level index signal derived from the raw sensor is then used, in conjunction with a selected Slope parameter, to point to a particular sensor-indicated rate (SIR) signal. The SIR signal may then be used by the pacemaker to define a pacing rate.

In order to prevent inappropriate increases in pacing rate while a patient is at rest or at low levels of activity, the '052 patent offers a plurality of programmable sensor rate response threshold values. The selected sensor response threshold value represents a minimum level of patient activity that must occur before the raw sensor signal is considered sufficiently large to represent meaningful physiological activity that should increase the SIR signal. One embodiment disclosed in the '052 patent provides for the automatic setting of the sensor rate response threshold by averaging the sensor index signal over a prescribed period to time and by adding thereto a fixed threshold offset value. In a preferred embodiment, the '052 patent teaches that the sensor level index signals be averaged over a preceding 18 hour period, and that a fixed offset of two (2) be added. (Note, that as used herein the sensor "offset" is measured in sensor units, which are relative units related to the maximum raw sensor output signal. For example, the full scale sensor output may be represented by 13 sensor units.)

Unfortunately, while the "autothreshold" feature of the invention disclosed in the '052 patent represents a valuable tool for a physician to use in programming the parameters of a rate-responsive pacemaker, the fixed sensor offset that is added to the 18 hour average as taught in the '052 patent makes such autothreshold feature impractical and undesirable for most patients. This is because a fixed offset, even when added to an automatically adjustable threshold, does not invoke the same pacemaker behavior in different patients. A sensor threshold and offset that provides ideal performance in one patient may be over response or under-responsive in another patient, or even for the same patient at a future time. Thus, each patient is unique, and requires a highly customized and versatile setting of the sensor rate response threshold and offset. What is needed, therefore, is a more versatile way of conditioning the raw sensor signal to fit the needs of a particular patient over time, and a way of programmably and/or automatically setting the "offset" that is used in conjunction with determining a sensor threshold.

The present invention advantageously addresses the above and other needs.

SUMMARY OF THE INVENTION

The present invention provides a way for a rate-responsive pacemaker to automatically determine when the magnitude of a sensor input signal, generated by a physiological sensor as a result of sensing a prescribed physiological parameter, is sufficiently large to evidence significant physiological activity to justify an increase in the pacing rate of the pacemaker. In accordance with the invention, the raw sensor signal is preliminary processed to produce a sensor input signal during each pacing cycle. In the autothreshold mode, a long-term running average of the sensor input signal is continuously maintained. The long-term running average of the sensor input signal is used as a baseline threshold value. A programmable offset is then added to the baseline threshold value. Any sensor input signal that exceeds the baseline threshold plus the programmable offset is considered to be sufficiently large to effect an increase in the pacing rate.

The use of the programmable offset advantageously makes the rate-responsive pacemaker non-responsive to small changes in the sensor input signal, yet still allows such changes to be included in the overall determination of an appropriate long-term average of the sensor input signal.

In operation, a suitable long-term average of the sensor input signal is computed as an average of the last n short-term averages of such sensor input signal, where n is a large integer, e.g., greater than 30. (Alternately, instead of using short-term averages, the raw or processed signal could also be used.) A short-term average of the sensor input signal may comprise, for example, the sensor input signal as filtered, or otherwise processed, over the previous pacing cycle. Alternatively, a short-term average may comprise m consecutive samples of the sensor input signal, where m is a small integer, e.g., 3–10. The short-term average thus provides a means of smoothing or filtering the raw sensor signal, and the sensor input signal may thus generally be considered as the smoothed or filtered raw sensor signal.

The long term average provides a baseline threshold ("T") reference value. In accordance with the present invention, a programmable offset ("O") value is added to the baseline threshold reference value to produce a threshold plus offset ("T+O") reference value. A given short-term average of the sensor input signal, i.e., a given sensor reading, must be greater than the T+O reference value before the sensor input signal is considered sufficiently large to evidence significant physiological activity. In other words, unless a given short-term average of the sensor input signal is greater than the threshold plus offset reference value, the sensor input signal, including the minor variations and fluctuations therein, are not considered by the rate-responsive sensor processing circuits, just as if no physiological activity had been sensed.

The value of the offset may be determined in various ways. In one embodiment of the invention, for example, the offset is programmable, and may be programmed to assume one of a plurality of values, e.g., 0, 0.5, 1.0, or 1.5 sensor units, where a full scale (maximum value of the raw sensor signal) is roughly 13 sensor units. In another embodiment of the invention, the offset is automatically determined as a function of the peak values of the short term raw sensor signal averaged over the last n short term averages, i.e., as a function of the peak values of the sensor readings over the last n sensor readings, where n is a large integer.

One embodiment of the present invention may be characterized as an implantable rate-responsive pacemaker. Such rate-responsive pacemaker includes: (1) physiological sensing means for sensing a physiological parameter and generating a raw sensor signal as a function of the sensed physiological parameter; (2) pre-processing means for processing the raw sensor signal and converting it to a sensor input signal; (3) means for computing a long-term average of the sensor input signal; (4) means for adding a programmably selectable offset to the long-term average so as to provide a Threshold value; (5) threshold means for determining when the sensor input signal exceeds the Threshold value; and (6) means responsive to the threshold means for providing stimulation pulses on demand at a pacing rate determined by a programmably selectable Slope value and the amount by which the sensor input signal exceeds the Threshold value.

Another embodiment of the invention may similarly be characterized as an implantable rate-responsive pacemaker. In this embodiment, the rate-responsive pacemaker is characterized as including: (1) a physiological sensor that senses a physiological parameter and generates a sensor input signal as a function of the sensed physiological parameter; (2) an averaging circuit that computes a long-term average of the sensor input signal; (3) a threshold circuit that determines when the sensor input signal exceeds the long-term average of the sensor input signal plus a selectable offset value; and (4) a pulse generator responsive to the threshold circuit that provides stimulation pulses on demand at a pacing rate determined by a programmably selectable Slope value and the amount by which the sensor input signal exceeds the long-term average of the sensor input signal plus the selectable offset value.

Yet another embodiment of the invention may be characterized as a method of automatically setting the Threshold value of a rate-responsive pacemaker. The rate-responsive pacemaker used with such method has a physiological sensor that senses a physiological parameter and generates a sensor input signal as a function thereof. The Threshold value is used by the rate-responsive pacemaker to provide a reference value that the sensor input signal must exceed before such sensor input signal is considered as evidence of significant physiological activity to which the rate-responsive pacemaker should respond. The method in accordance with this embodiment includes the steps of: (a) processing the sensor input signal over a prescribed time period to provide a reference sensor input signal that is representative of the sensor input signals during the prescribed time period; (b) programmably selecting one of a plurality of offset values; and (c) adding the offset value selected in step (b) to the baseline reference sensor input signal determined in step (a) to obtain the Threshold value.

Thus, it is a feature of the present invention, in accordance with one embodiment thereof, to provide a rate-responsive pacemaker wherein a programmable offset is added to an automatically generated baseline threshold value in order to define a Threshold level above which the sensor input signal of the rate-responsive pacemaker must go before such sensor input signal is considered as evidence of significant physiological activity.

It is another feature of the invention, in accordance with another embodiment thereof, to automatically determine an offset that is added to an automatically generated baseline threshold value in order to define a Threshold level above which the sensor input signal of the rate-responsive pacemaker must go before such sensor input signal is considered as evidence of significant physiological activity.

It is an additional feature of the invention to provide a programmable rate-responsive pacemaker that may be selectively programmed to provide either: (1) an automatically generated baseline threshold, to which a selected one of a plurality of offset values may be added, or (2) a programmed threshold value selected from a plurality of fixed baseline threshold values, to which no offset is added, in order to define the sensor Threshold level of the pacemaker. The sensor Threshold level of the pacemaker, as above, is that threshold reference level which must be exceed by the sensor input signal before it is considered as an indication of significant physiological activity.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The present invention relates to a rate-responsive pacemaker having an automatic sensor threshold with a programmable offset. Before describing the invention, and in order to better understand the description of the invention that follows, it will first be helpful to have a basic understanding of how a rate-responsive pacemaker operates, as well as an understanding of how such a pacemaker is programmed. Accordingly, an overview of the operation of a rate-responsive pacemaker will first be presented, including a description of the programmable sensor parameters that are used with such a rate-responsive pacemaker. More complete details associated with the rate-responsive pacemaker used with the present invention, as well as the preferred programmer used to program such pacemaker may be found in U.S. Pat. Nos. 4,809,697 and 4,940,052. The '697 patent is incorporated herein by reference. (The '052 patent has already been incorporated herein by reference.) Further, additional details associated with some related features of the present invention may be found in the following copending and commonly owned U.S. patent applications: (1) Ser. No. 07/846,461, filed concurrently herewith, entitled METHOD AND SYSTEM FOR RECORDING AND REPORTING THE DISTRIBUTION OF PACING EVENTS OVER TIME; (2) Ser. No. 07/846,460, filed concurrently herewith, entitled METHOD AND SYSTEM FOR RECORDING AND REPORTING A SEQUENTIAL SERIES OF PACING EVENTS; and (3) Ser. No. 07/844,818, also filed concurrently herewith, entitled METHOD AND SYSTEM FOR AUTOMATICALLY ADJUSTING THE SENSOR PARAMETERS OF A RATE-RESPONSIVE PACEMAKER. Each of the above-identified U.S. Patent Applications are also incorporated herein by reference.

Figure 1:
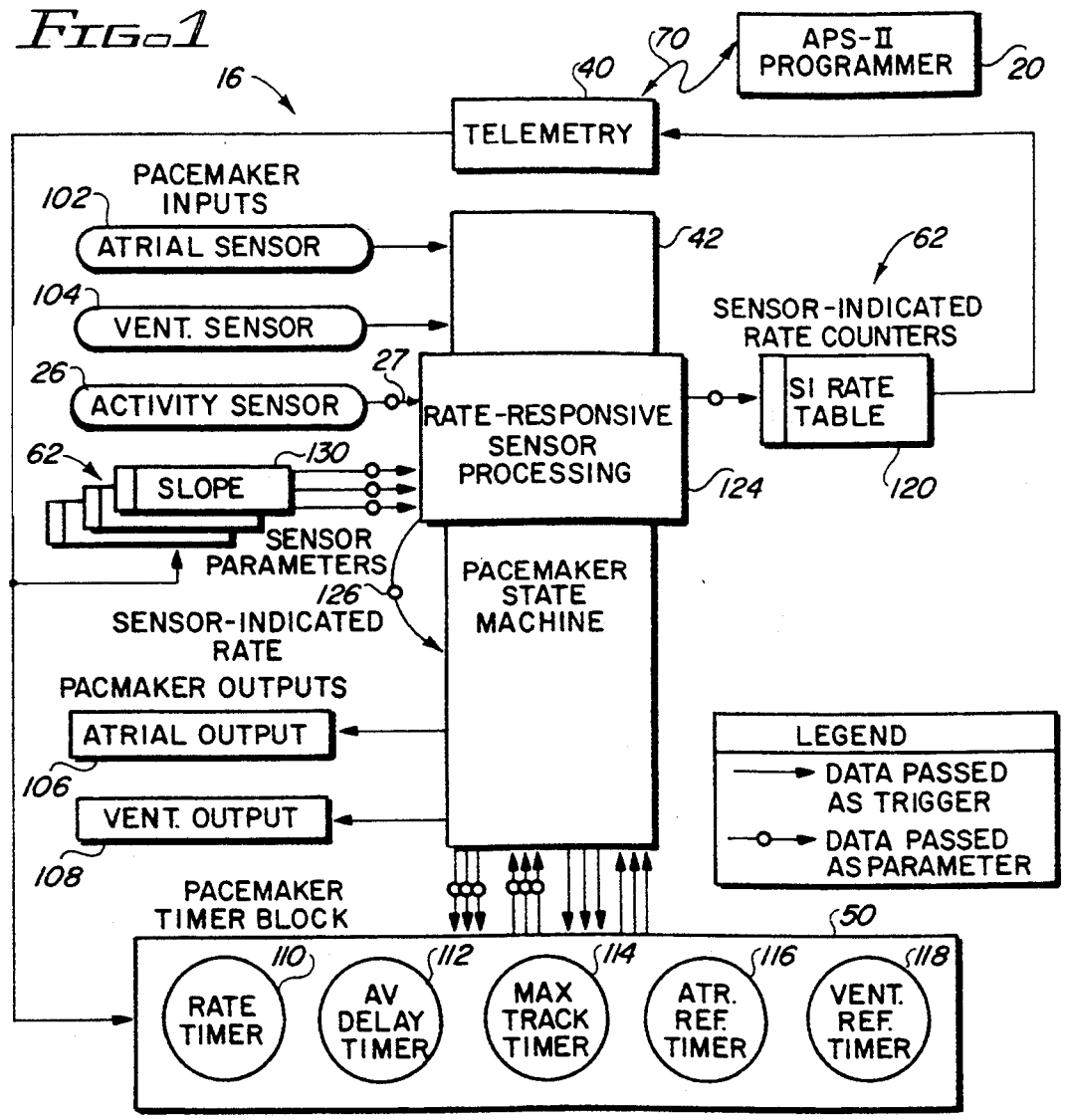
FIG. 1 shows a block diagram of a rate-responsive pacemaker.

Referring first to FIG. 1, there is shown a functional block diagram of a rate-responsive pacemaker 16 that illustrates the manner in which the pacemaker operates. The pacemaker 16 includes pacemaker state logic 42, also referred to as the pacemaker state machine. Coupled to the state machine 42 are pacemaker timer circuits 50, also referred to as the pacemaker timer block. The pacemaker 16 receives as inputs, i.e., signals sensed by the pacemaker that are not programmed, signals from an atrial sensor 102 and a ventricular sensor 104. The atrial sensor 102 and ventricular sensor 104 sense P-waves and R-waves, evidencing the natural contraction of the atria or ventricles, respectively. The atrial sensor 102, for example, may include an atrial tip electrode, an atrial lead 31 (not shown) and atrial channel amplifier 48 (not shown). Similarly, the ventricular sensor 104 may comprise a ventricular tip electrode, a ventricular lead and a ventricular amplifier.

The inputs to the rate-responsive pacemaker 16 also include a raw sensor signal 27 obtained from a physiological sensor 26. (It is noted that while only a single physiological sensor 26 is shown in FIG. 1, more than one such sensor may be used, each providing its own sensor input.) The raw sensor signal 26 is input to a rate-responsive sensor processing circuit 124. After appropriate processing, as described more fully below, the sensor processing circuit 124 provides a sensor indicated rate (SIR) signal 126 to the pacemaker state machine 42.

In addition to the above-described pacemaker inputs, there are several pacemaker control parameters that are input to the pacemaker state machine 42 in order to control its operation in a desired fashion. Such control parameters are normally programmed into the pacemaker 16 using an external programmer 20, such as the APS-II/MTM external programmer manufactured by Siemens Pacesetter, Inc. of Sylmar, Calif., that establishes a telemetry link 70 with a telemetry circuit 40 included within the pacemaker 16.

The parameters programmed into the pacemaker are typically stored in a memory 62 of the pacemaker 16. (The memory 62 is not shown as a separate block in FIG. 1, but it is to be understood that the programmed parameters may be held in such memory, as may output data generated by the pacemaker that is to be telemetered to the programmer 20.) Such control parameters include, e.g., the programmed rate at the which the stimulation pulses are to be generated by the pacemaker (used to define various time periods within the timer block 50), the particular mode of operation of the pacemaker, a set of sensor control parameters 130 (described below), and the like.

The rate-responsive pacemaker outputs, i.e., signals generated by the pacemaker state machine 42 in response to the pacemaker inputs and/or pacemaker control parameters include an atrial output 106 and a ventricular output 108. The atrial output 106 provides an atrial stimulation pulse ("A-pulse") for delivery to the atrium at an appropriate time, e.g., on demand as needed to maintain a programmed or sensor-indicated heart rate. The ventricular output 108 similarly provides a ventricular stimulation pulse ("V-pulse") for delivery to the ventricle at an appropriate time, e.g., on demand as needed to maintain a programmed or sensor-indicated heart rate.

The pacemaker timer circuits 50 include at least five separate timers. A rate timer 110 determines or measures the pacing cycle duration. An AV Delay Timer 112 defines the time period between an A-pulse and a V-pulse. A Max Track Timer 114 defines the time period of the maximum rate at which the pacemaker is allowed to provide stimulation pulses, i.e., it defines the maximum paced rate. An Atrial Refractory Timer 116 defines the atrial refractory period (i.e., that time period during which the atrial channel is refractory). Similarly, a Ventricular Refractory Timer 118 defines the ventricular refractory period, or that time during which the ventricular channel is refractory.

Note from the symbols used in FIG. 1 that two kinds of data are passed to and from the pacemaker state machine 42. Such data may take the form of a trigger signal or a parameter signal. A trigger signal, represented by an input line with an arrow pointing the direction of flow of the trigger data, is a signal that operates substantially immediately, much like an interrupt signal, to bring about a desired result. That is, for example, immediately upon sensing atrial activity through the atrial sensor (or within a few clock cycles thereafter, where a clock cycle is typically on the order of a few microseconds), the state of the state machine 42 changes appropriately to bring about a desired result. In contrast, a parameter signal, represented by an input line passing through a circle with an arrow pointing the direction of flow of the parameter data, is a signal that is made available to the state machine 42 for use at the appropriate time during the normal timing cycle of the state machine.

In accordance with the present invention, the rate-responsive sensor processing circuits 124 receive the raw signal 27 from the sensor 26 and derive a SIR signal 126 therefrom based on a set of sensor control parameters 130. The SIR signal 126 may then be used by the state machine 42, if so programmed, to control the rate at which stimulation pulses are provided to the heart on demand through the atrial or ventricular outputs 106 and 108. The SIR signal 126 is sampled at a fixed, but programmable rate (which may be, e.g., every event, every 1.6 seconds, or every 26 seconds). The SIR signal as sampled may be classified by rate and stored in an SIR Table 120. (The SIR Table 120, which effectively accumulates SIR Histogram and Event Record data, is described more fully in one of the above referenced copending patent applications, and is also described in the '052 patent cited above.)

The SIR Histogram Table 120 and the beneficial use of the data stored therein is not the subject of the present invention. Rather, the present invention relates to the manner in which the SIR signal is derived from the raw sensor signal 27. More particularly, the present invention relates to the manner in which a determination is made as to whether the raw sensor signal is of sufficient magnitude to evidence significant physiological activity. As explained below, such determination is made as controlled by one or more programmed sensor control parameters.

Figure 2:
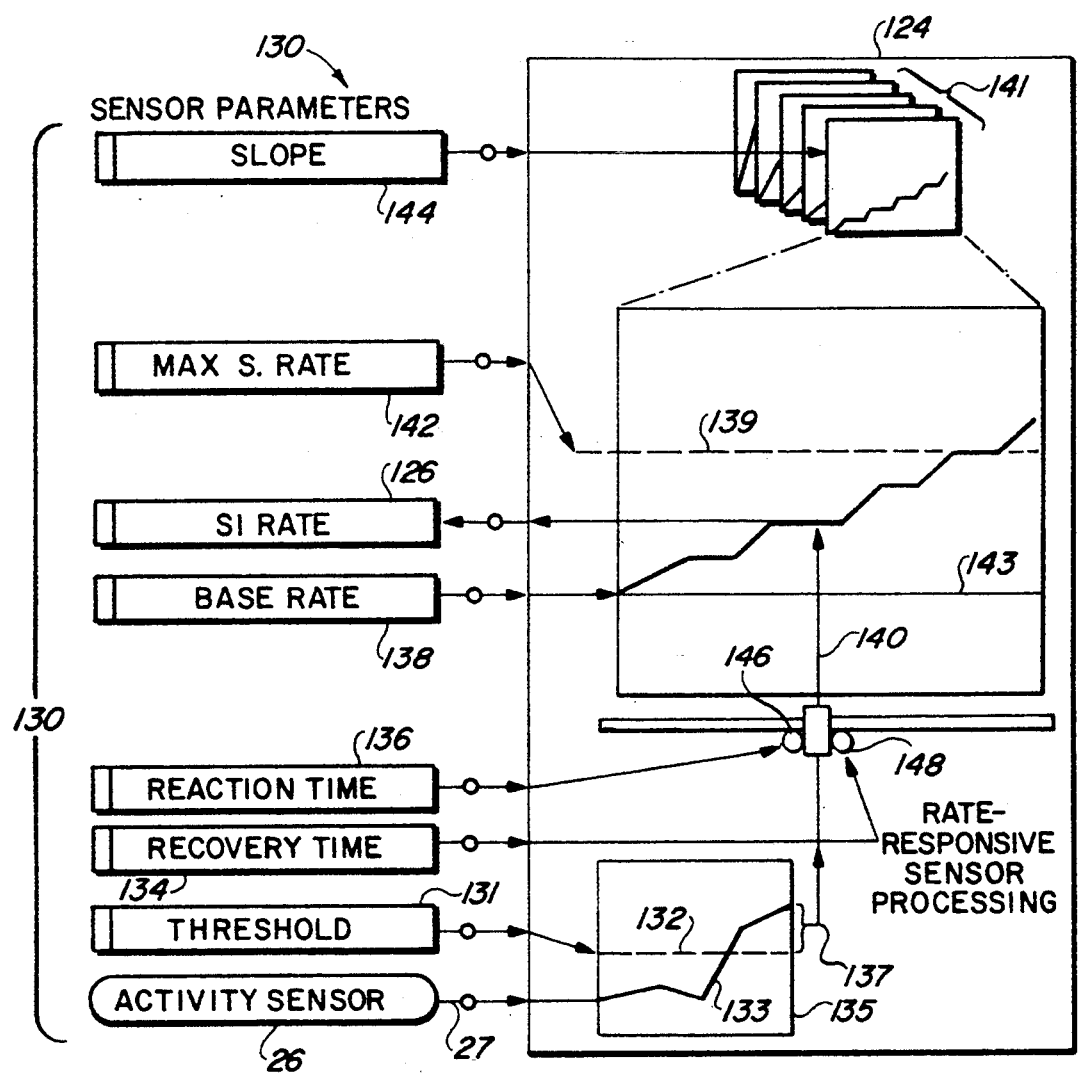
FIG. 2 is a block diagram of the rate-responsive processing subsystem of FIG. 1, and functionally illustrates the parametric controls used to adjust the sensor indicated rate (SIR) signal as a function of the sensor input signal.

The sensor control parameters that may be programmed in a rate-responsive pacemaker 16 are functionally illustrated in FIG. 2. FIG. 2 shows a functional block diagram of the rate-responsive processing subsystem 124 of the rate-responsive pacemaker 16 of FIG. 1. FIG. 2 shows the set of sensor control parameters 130 that are used in deriving the sensor indicated rate (SIR) signal 126. FIG. 2 further diagrammatically illustrates how such derivation is accomplished as a function of the raw sensor signal 27.

As seen in FIG. 2, there may be up to six sensor control parameters that are programmably selected. Such programmable sensor control parameters may thus be considered as inputs to the rate-responsive processing subsystem 124. These six sensor control parameters are: a Threshold parameter 131 (which, as explained below, may be selected to be an autothreshold value with a programmable offset); a Recovery Time parameter 134; a Reaction Time parameter 136; a Base Rate parameter 138; Maximum Sensor Rate parameter 142; and Slope parameter 144. As also seen in FIG. 2, there is one output parameter: a Sensor Indicated Rate (SIR) parameter or signal 126. These parameters are explained more fully below.

The sensor 26 (which is illustrated in FIG. 1 and FIG. 2 as an "activity sensor"; but which may be another type of physiological sensor, or combination of physiological sensors) generates a raw signal 27 in response to detected physiological stress in the patient. The raw signal 27 is processed in an appropriate manner, e.g., to determine the energy content thereof as taught in U.S. Pat. No. 4,940,053, in order to provide a suitable sensor input signal 133 that may be processed by the rate-responsive sensor processing subsystem 124. (The '053 patent is also incorporated herein by reference.) The processed sensor input signal 133 will thus vary as a function of time, as suggested by the graph 135, as the physiological stress of the patient varies as detected by the sensor 26. (Note that this signal 133 is termed a "sensor input signal" because it is input into the rate-responsive sensor processing subsystem.)

The Threshold parameter 131 defines the level above which the sensed physiological stress, e.g., activity, must rise before it is considered significant. Once the stress level has risen above this level, referred to as the Threshold 132 (and represented in FIG. 2 as a dotted line 132), then the amount that it exceeds the Threshold 132 is used as an input to the rate-responsive sensor processing subsystem 124. This signal amount (the signal amount above the Threshold 132) is schematically represented in FIG. 2 as the bracketed area 137 for the time corresponding to the right edge of the graph 135. As described more fully below, the present invention relates to the specific manner in which the signal amount 137 is determined at any given time. More particularly, as will be evident from the description presented below in conjunction with FIGS. 3-6, the present invention provides a means whereby the Threshold 132 may be automatically set based on a long-term average of the sensor input signal 133 and a programmable offset value that is added to such long-term average.

Still referring to FIG. 2, the Slope parameter 144 defines the relationship between the amount the sensor input signal is above the Threshold 132, if any, and the increase or decrease in pacing rate. That is, the Slope parameter may be considered, as its name implies, as a curve or transfer function that converts that portion 137 of the sensor input signal above the Threshold level to the sensor indicated rate (SIR) signal 126. It should also be pointed out that if the sensor input signal is not above the Threshold level, then that fact too may influence the determination of the SIR signal 126. That is, if the sensor input signal is not above the Threshold 132, then that evidences, in effect, a zero sensor input signal (i.e., the lack of significant physiological activity). The lack of sensed physiological activity, as explained below, can cause the SIR signal to decrease to the base rate.

There are a multiplicity of possible Slope parameters or curves 144 that may be programmably selected, each one providing a different rate increase in response to sensed physiological stress above the Threshold. Such multiplicity of Slope parameters 144 are schematically represented in FIG. 2 as the family of Slope curves 141.

The Maximum Sensor Rate parameter 142 defines the upper limit of the rate range of the rate-responsive pacemaker 16. The pacemaker will not pace above this rate, regardless of the amount by which the sensor input signal exceeds the Threshold 132. Such upper limit is schematically represented in FIG. 2 as the dotted line 139.

The Base Rate parameter 138 defines the lower limit of the rate range of the rate-responsive pacemaker 16. The pacemaker will not pace below this rate, even if the sensor input signal is below the Threshold 132. When the pacemaker is pacing at the base rate, the patient is at rest or undergoing physiological stress at a level below the Threshold 132. Such lower limit is schematically represented in FIG. 2 as the solid line 143.

Still referring to FIG. 2, the Reaction Time parameter 136 determines the minimum time to be allowed for an increase in pacing rate from the Base Rate to the programmed Maximum Rate. The Reaction Time controls the amount of time the pacemaker spends at a given pacing rate by requiring a minimum number of stimulation pulses at that rate. Once these pulses occur, the rate can be increased. A short Reaction Time allows the pacing rate to accelerate rapidly in response to sensed physiological activity above the Threshold; a long Reaction Time forces a slow increase in the pacing rate.

The Recovery time parameter 134 determines the minimum time allowed for a decrease in pacing rate from the programmed Maximum Rate 142 to the Base Rate 138. It uses the same principle as the Reaction Time. That is, it controls the amount of time the pacemaker spends at a given pacing rate by requiring a minimum number of stimulation pulses before the rate can be decreased. A short Recovery Time allows a rapid deceleration of the pacing rate; a long Recovery Time forces a slower decrease in pacing rate.

In operation, the sensor 26 senses physiological activity and generates a raw signal 27 in response thereto. The raw signal 27 is processed in an appropriate manner in order to produce the sensor input signal 133. The amount 137 by which the sensor input signal 133 exceeds the Threshold 132, in conjunction with the Reaction Time 136, provides a sensor index signal 140 that points to a specific entry point on one axis of the selected Slope curve 144. The Reaction Time 136 determines how rapidly the sensor index signal moves along the selected Slope curve 144 towards the Maximum Rate 139. If the number of pulses at the current SIR signal 126 has reached the amount required by the Reaction Time, the SIR may be increased to its next value, as defined by the current value of the SIR rate 126, and limited by the Maximum Sensor Rate 139. If the Reaction Time pulse count has not been reached, the SIR signal will not change.

If no sensor input signal is detected as being above the Threshold 132, and if this lack of activity has occurred for the number of pulses specified by the Recovery Time parameter, the SIR signal may be decreased to its next value as defined by the selected Slope curve and as limited by the Base Rate parameter 138. If the Recovery Time pulse count has not been reached, the SIR signal will not change.

Note, as described above, that the Reaction Time 136 controls the rate of increase of the SIR signal 126, and hence the rate of increase of the pacing rate. The Recovery Time 134 controls the rate of decrease of the SIR signal 126, and hence the rate of decrease of the pacing rate. The Reaction Time 136 is schematically illustrated in FIG. 2 as a roller 146 that controls how fast the sensor index signal 140 is allowed to move left-to-right along the horizontal axis of the selected Slope curve 144. Similarly, the Recovery Time 134 is schematically illustrated in FIG. 2 as a roller 148 that controls how fast the sensor index signal 140 is allowed to move right-to-left along the horizontal axis of the selected Slope curve 144.

In accordance with the present invention, the Threshold 132, i.e., that level above which the sensor input signal must reach before such sensor input signal is considered as representing significant physiological activity, may be programmably set in one of two ways. First, the Threshold 132 may be set to one of a plurality of fixed values. Second, the Threshold 132 may be programmed to be set automatically with a selected "offset" value added thereto. For convenience of explanation, the sensor input signal 133 is considered as ranging from 0 to 13 sensor units, with a value of 13 representing the maximum possible sensor input signal (i.e., the highest possible physiological activity), and with a value of 0 representing the minimum possible sensor input signal (i.e., no sensed physiological activity).

With the sensor units defined as indicated above, the rate-responsive pacemaker of the present invention allows the Threshold control parameter 131 to be selectively programmed to one of the values indicated in Table 1. Note that the first four values listed in Table 1 are considered as "autothreshold" values. When one of the autothreshold values are selected, the Threshold 132 is determined by computing a long-term average of the sensor input signal 133, e.g., an 18 hour average, and by adding the indicated offset to such long-term average. When one of the fixed threshold values are selected, then the Threshold 132 assumes the value selected, and does not change.

TABLE 1

| Threshold Value | Offset |
|---|---|
| AUTO +0.0 | +0.0 |
| AUTO +0.5 | +0.5 |
| AUTO +1.0 | +1.0 |
| AUTO +1.5 | +1.5 |
| 1.0 (low) | None |
| 1.5 | None |
| 2.0 | None |
| 2.5 | None |
| 3.0 | None |
| 3.5 | None |
| 4.0 | None |
| 4.5 | None |
| 5.0 | None |
| 5.5 | None |
| 6.0 | None |
| 6.5 | None |
| 7.0 (high) | None |

Figure 3:
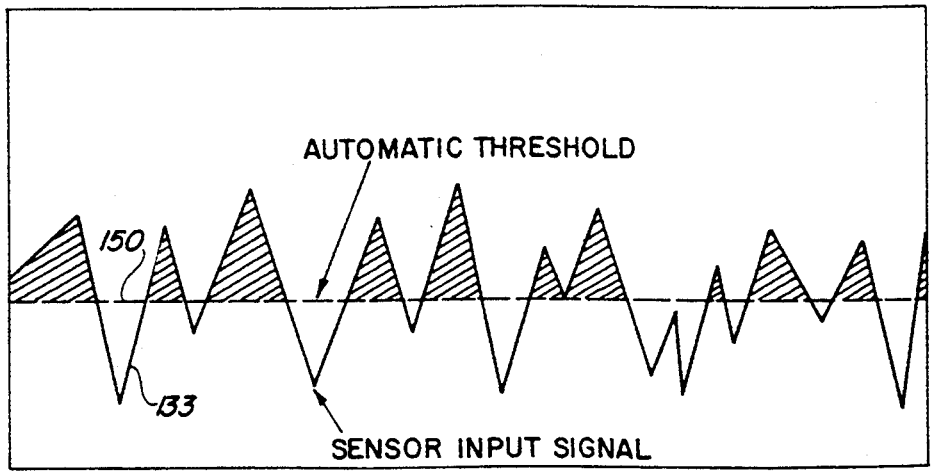
FIG. 3 shows a typical sensor input signal and an automatic threshold level determined as a long-term average of the sensor input signal.

Referring next to FIG. 3, a representation of the sensor input signal 133 is shown as it might appear as a function of time. Note that the signal 133 dithers and varies a great amount, as would be expected for a typical sensor input signal. Also shown in FIG. 3 is a representation of a running long-term average (shown as a dotted line 150) of the sensor input signal 133. By definition, over the long-term there are an equal number of excursions of the sensor input signal 133 above the long-term average 150 as there are excursions below the long-term average 150. If the long-term average 150 were used as the Threshold 132, then any of the excursions above the average 150, represented as the shaded portion of the excursions, would cause the sensor index signal 140 (FIG. 2) to be erratically active, potentially causing too much sensitivity to low activity resulting in increases in the SIR signal 126 (although such changes could be tempered by proper programming of the Reaction and Recovery time sensor control parameters described above).

Figure 4:
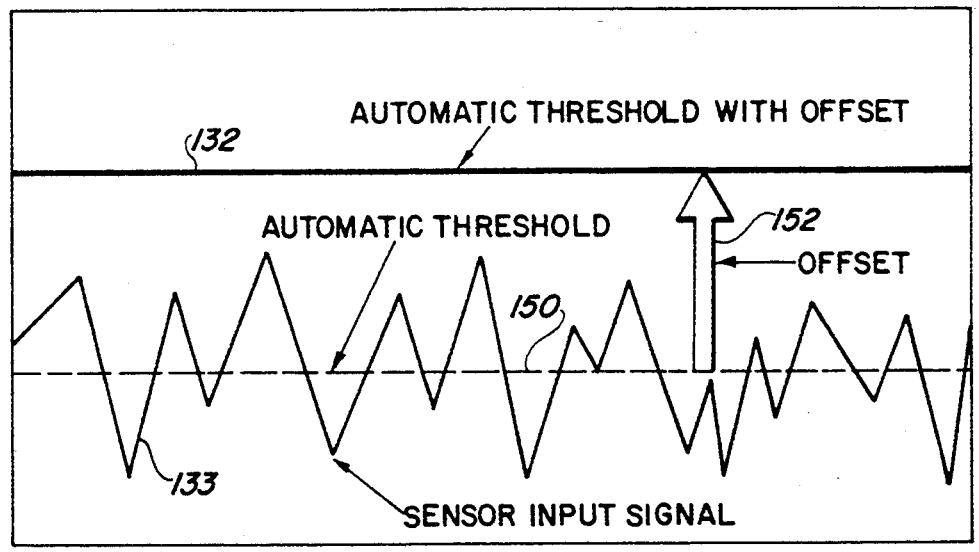
FIG. 4 shows a typical sensor input signal and automatic threshold level as in FIG. 3, and further conceptually illustrates the use of an offset value that is added to the automatic threshold level.

To minimize oversensitivity of increases in the sensor index signal, the present invention advantageously utilizes a programmable offset 152 that is added to the long-term average 150 as shown in FIG. 4 whenever an autothreshold value is programmably selected as the Threshold parameter 131. As indicated in Table 1, there are four possible offset values that may be selected when the autothreshold feature is selected. It is to be understood, however, that this is merely exemplary, as any number of offset values, having a wide range of values, could be made available for selection. Thus, by defining the Threshold level 132 (which the sensor input signal 133 must exceed in order to be considered as evidence of significant physiological activity) as the long-term average 150 plus the offset value 152, most of the minor and inconsequential fluctuations of the sensor input signal 133 are advantageously ignored insofar as influencing the sensor index signal 140 is concerned.

However, all such fluctuations still contribute to the long-term average 150.

In accordance with an alternative embodiment of the present invention, the offset value 152 that is added to the long-term average of the sensor input signal 133 may also be automatically determined. Such automatic determination may be based on any suitable processing routine. For example, the value of the offset 152 may be automatically determined as the long-term average of the peak values of the sensor input signal. Alternatively, the offset value 152 may be automatically determined as the peak-to-peak variation in the long-term average of the sensor input signal. Indeed, any processing method or technique that defines a meaningful offset value 152 that may to added to the long-term average of the sensor input signal 133 may be used.

Figure 5:
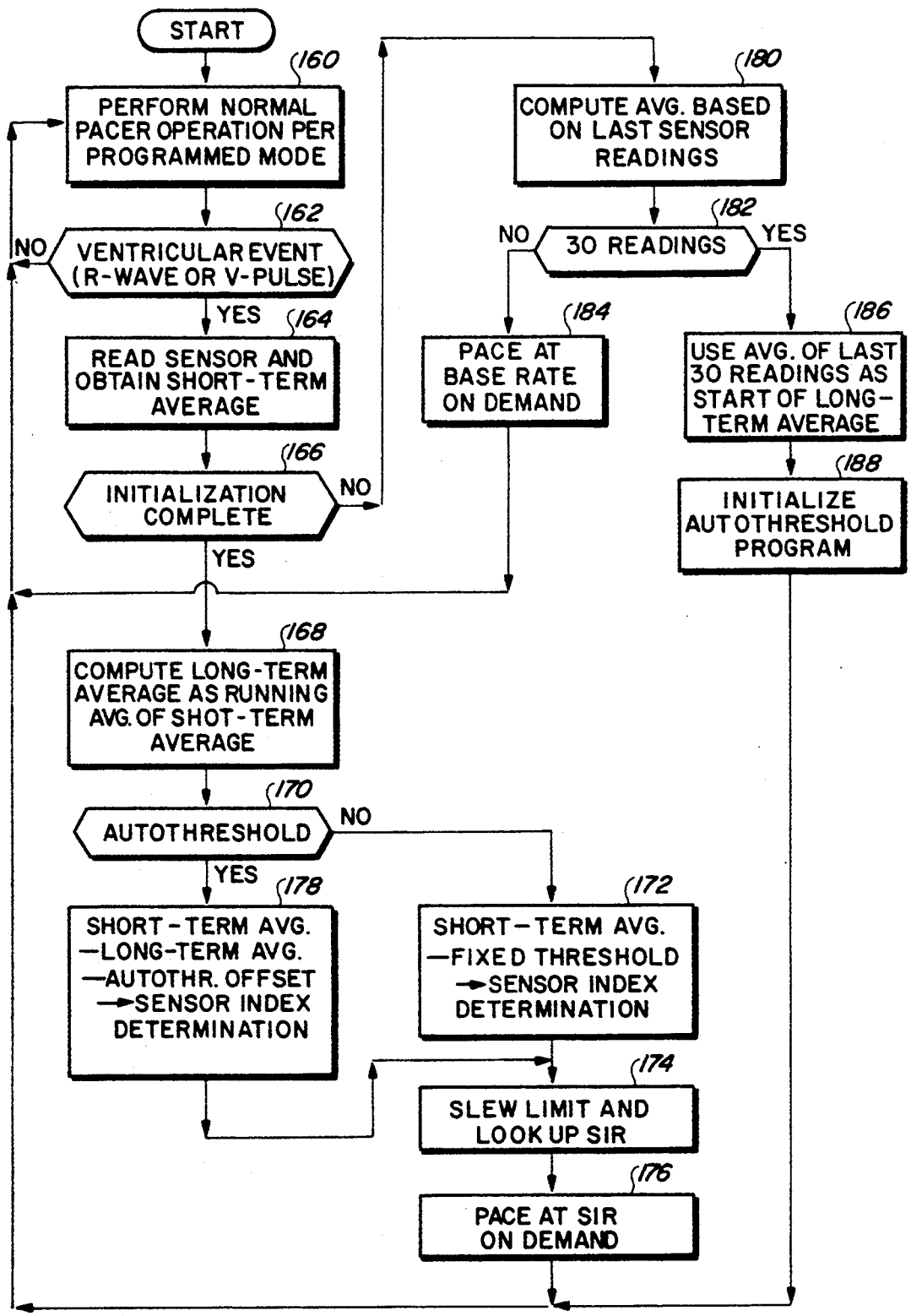
FIG. 5 is a flow chart that illustrates the manner in which the autothreshold feature of the present invention is used in order to arrive at a sensor level index signal, which sensor level index signal is used in conjunction with a Slope parameter to define a sensor indicated rate (SIR) signal for use by the rate-responsive pacemaker.

Referring next to FIG. 5, there is shown a flow chart that illustrates the manner in which the autothreshold feature of the present invention is utilized in order to arrive at a sensor level index signal, which sensor level index signal is used in conjunction with a Slope parameter to define a sensor indicated rate (SIR) signal for use by the rate-responsive pacemaker. In the flow chart of FIG. 5, each main step is illustrated as a block, or box, with each block having a corresponding number assigned thereto for reference purposes.

As seen in FIG. 5, the present invention is invoked (when programmably selected) during the normal programmed operation of the pacemaker (or "pacer"). That is, the pacer operates in its programmed mode of operation in a normal manner (block 160). When, during the course of its programmed mode of operation, a ventricular event occurs (block 162), the sensor input signal is read in order to obtain a short-term average thereof (block 164). A short-term average is typically considered as a single reading of the sensor 26 (FIG. 1), which reading normally occurs once during each pacing cycle. A short-term average of the sensor signal may thus comprise the raw sensor signal as filtered, or otherwise processed, over the previous pacing cycle. That is, during the course of processing the raw sensor signal 27 to produce the sensor input signal 133, as will be explained below in conjunction with FIG. 6, the raw sensor signal is typically amplified, rectified and filtered, all of which tends to average or smooth the raw sensor signal. Such filtering and averaging is highly advantageous because the raw sensor signal itself can be highly erratic and unstable. Hence, in the normal process of obtaining the sensor input signal 133, an effective short-term average of the raw sensor signal is obtained (block 164).

Alternatively or conjunctively, in some embodiments of the invention it is desirable to sample the sensor input signal at a prescribed sampling rate, e.g., once each ventricular or atrial event, and average the samples over a relatively short time period or number of samples in order to produce a short-term average. A short-term average may thus comprise m consecutive samples of the sensor input signal, where m is a small integer, e.g., 3–10; or m consecutive samples of the raw sensor signal.

After the short-term average of the raw sensor signal and/or the sensor input signal has been obtained (block 164), a determination is made as to whether a sufficient number of short-term averages have been obtained to provide a meaningful long-term average (block 166). That is, there must be some initialization process invoked in order to provide sufficient data for a long-term average to be computed. Thus, if such initialization has not been completed (block 166), then an average is computed based on whatever sensor readings have been made (block 180). Unless thirty (30) sensor readings have thus been taken (block 182), the pacemaker paces at the Base Rate (block 184), i.e., the pacemaker provides stimulation pulses on demand to either the atrium and/or the ventricle at the programmed Base Rate in accordance with the normal pacemaker operation in the programmed mode (block 160).

If thirty (30) sensor readings have been included in the computation of the average of the sensor input signal (made at block 180), as determined at block 182, then such computed average is used as the start of a long-term average (block 186), and the initialization of the autothreshold program is deemed completed (block 188). Thereafter, upon continuing with the normal pacer operation (block 160), and updating the sensor short-term average (block 164), the determination is made that the initialization is complete (block 166). With the initialization complete, a long-term average of the sensor reading is begun by maintaining a running average of the short-term averages (block 168). That is, the sensor reading, or the sensor input signal, continues to be averaged over a specified number of pacing cycles or a specified time period. In the preferred embodiment, such running average is maintained for 18 hours. That is, the long-term average of the sensor input signal reflects the most recent 18 hours of operation, with the most current sensor reading always being included in the long-term average computation, and the oldest sensor reading (i.e., the one that occurred just over 18 hours ago) being deleted from the computation. Thus, it is seen that the long-term average of the sensor input signal is computed as an average of the last n short-term averages of such sensor input signal, where n is a large integer, e.g., greater than 30.

At this point, it should be noted that other measures of the sensor input signal, in addition to, or in place of, a long-term average, could also be used. For example, a weighted average of the sensor input signal could be performed, giving greater weight to the sensor input signals from certain time periods of the day. Further, a least squares computation could be performed wherein the sensor input signals having a large variance from other sensor input signals are discounted. In other words, any processing method or technique that provides a meaningful measure of the variation and movement of the sensor input signal over the long-term time period of interest may be employed.

Still referring to FIG. 5, after the long-term average has been updated with the most recent short-term average (block 168), a determination is made as to whether one of the autothreshold values has been selected (block 170). If not, then that means a fixed Threshold parameter has been programmed. In such case, the sensor level index signal, which (in the preferred embodiment) is a discrete number ranging from 0 to 31, is derived from the short-term average, less the fixed Threshold value (block 172). Only if the short-term average is greater than the fixed Threshold value does a sensor level index signal result that is considered sufficiently large to evidence significant physiological activity.

If one of the autothreshold values has been selected (block 170), then the sensor level index signal is derived from the short-term average, less the long-term average, less the selected value of offset. (block 178). Thus, only if the short-term average (which, as indicated above, is typically the value of the sensor input signal for the current pacing cycle) is greater than the long-term average and the selected (programmed) offset value does a sensor level index signal result that is considered sufficiently large to evidence significant physiological activity.

Regardless of how the sensor level index signal is determined, whether using a fixed Threshold value (block 172) or an autothreshold value with offset (block 178), the sensor level index signal is then used in conjunction with a programmed Slope parameter, as described, e.g., in the '052 patent or one of the above-identified patent applications, to point to a sensor indicated rate (SIR) value (block 174). The SIR value is then used by the rate-responsive pacemaker, when operating in a rate-responsive mode, to determine the rate at which stimulation pulses are provided on demand (block 176).

Figure 6:
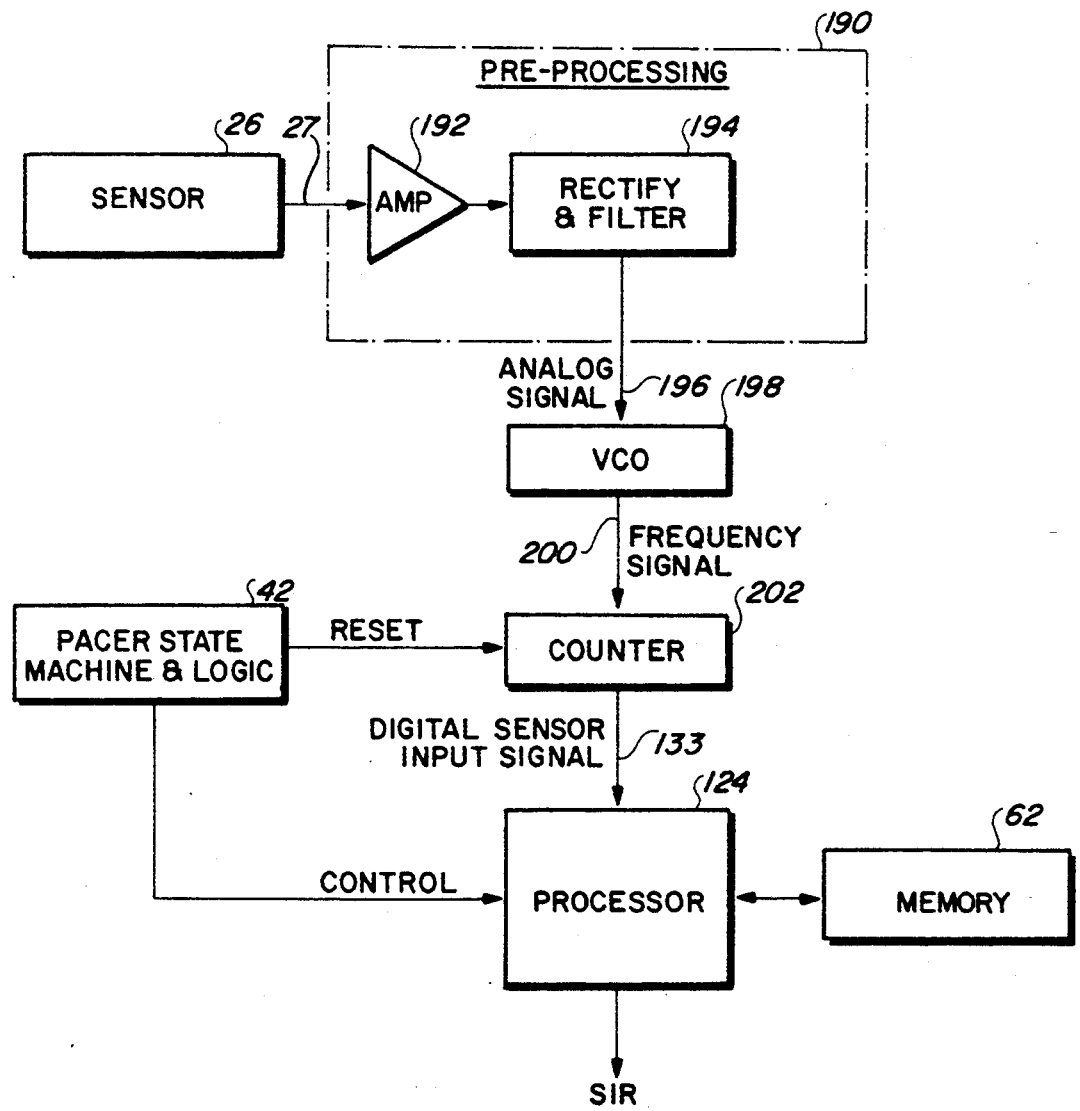
FIG. 6 is a block diagram that illustrates how the raw sensor signal is processed to provide a sensor input signal.

Turning next to FIG. 6, there is shown a block diagram that illustrates how the raw sensor signal 27 is processed to provide the sensor input signal 133. As seen in FIG. 6, the sensor 26, which in the preferred embodiment comprises a piezoelectric crystal, generates the raw sensor signal 27. The raw sensor signal 27 is processed in pre-processing circuitry 190 comprising an amplifier 192 and a rectification/filter circuit 194. The amplifier 192 has a bandwidth associated therewith that varies from about 0.8 to 40 Hz. The raw signal is rectified and filtered using the rectification/filter circuit 194 substantially as described in the '053 patent, or equivalent manner. Such rectification and filtering results in an analog signal 196 having an amplitude that varies as a function of the energy content of the raw sensor signal 27.

The analog signal 196 is coupled to a voltage-controlled oscillator (VCO) 198 which generates an output frequency signal 200 that is frequency modulated as a function of the analog signal 196. In the preferred embodiment, the VCO frequency increases as the absolute value of the voltage input to the VCO increases in magnitude, with the VCO frequency varying from about 0 Hz at 0 volts input (no activity sensed), to about 22 KHz at approximately $-2.66$ volts (high level of activity sensed). Thus, the frequency signal 200 has a frequency varying from about 0 Hz to about 22 KHz. It should be noted, however, that such VCO parameters are only exemplary, and that other parameters could also be used.

The frequency signal 200 is counted in a counter circuit 202. The counter circuit 202 is reset each sampling period, e.g., each pacing cycle, by the pacer state machine and related logic 42 of the rate-responsive pacemaker. The contents of the counter circuit 202 at the conclusion of each sampling period thus comprise a digital word. Such digital word functions as the sensor input signal 133 for that sample period. Such sensor input signal 133 may then be processed by the rate-responsive sensor processing circuits 124, as controlled by the sensor control parameters stored in the pacer memory 62, in order to perform the long-term averaging and offset addition in the manner programmed.

In the preferred embodiment, the counter 202 is an eight bit counter. Such counter may thus contain a count that ranges from 0 to 255. During a typical autothreshold operation, the sensor input signal 133, i.e., the count obtained from the counter 202, after appropriate scaling, is averaged over a sufficiently long-term, e.g., at least 30 samples and no more than 18 hours, to produce a running, long-term average. The long-term average is then subtracted from the current sensor input signal, as is the selected offset value, and the resulting number, after appropriate scaling and processing, becomes the sensor level index signal, having a value ranging from 0 to 31. The sensor level index signal, in turn, points to the appropriate SIR value as a function of the programmed Slope parameter.

As described above, it is thus seen that the present invention provides, in one embodiment, a rate-responsive pacemaker wherein a programmable offset value is added to an automatically generated baseline threshold value (long-term average) in order to define a Threshold reference level above which the sensor input signal of the rate-responsive pacemaker must go before such sensor input signal is considered as evidence of significant physiological activity. In another embodiment, the invention automatically determines an offset value that is added to an automatically generated baseline threshold value (long-term average) in order to define the Threshold reference level.

As further described above, it is seen that the invention provides a programmable rate-responsive pacemaker that may be selectively programmed to provide either: (1) an automatically generated Threshold value, comprising a long-term average to which a selected one of a plurality of offset values may be added, or (2) a programmed Threshold value selected from a plurality of fixed baseline threshold values, to which no offset is added. Such programmably selected Threshold levels thus provide a means for effectively defining that threshold reference level which must be exceed by the sensor input signal before it is considered as an indication of significant physiological activity. Hence, such programmable Threshold levels provide an effective tool in programming the rate-responsive pacemaker for optimum operation with respect to a given patient.

While the invention herein disclosed has been described by means of specific embodiments and applications thereof, numerous modifications and variations could be made thereto by those skilled in the art without departing from the scope of the invention set forth in the claims. For example, while the invention has been described substantially as a digital embodiment, particularly relative to the manner in which the sensor input signal is processed to produce a digital sensor input signal, and the manner in which the digital sensor input signal is processed to point to an appropriate SIR signal, such processing could also be carried out using equivalent analog circuitry, or hybrid circuitry (analog and digital).

What is claimed is:
1. An implantable rate-responsive pacemaker comprising:
   physiological sensing means for sensing a physiological parameter and generating a raw sensor signal as a function of the sensed physiological parameter;
   pre-processing means for processing said raw sensor signal, determining a short-term average thereof for a first prescribed time period, and converting the short-term average to a sensor input signal;
   means for computing a long-term running average of said sensor input signal over a second prescribed time period;
   means for automatically determining an offset value and adding said offset value to said long-term average so as to provide a threshold value;
   threshold means for determining when said sensor input signal exceeds said threshold value for determining a difference signal thereof as an output; and means, responsive to said threshold means, for providing stimulation pulses on demand at a pacing rate dependent upon said difference signal.

2. The rate-responsive pacemaker, as set forth in claim 1, further comprising:
timing means for determining said first prescribed time period, said first prescribed time period corresponding to at least one pacing cycle.

3. The rate-responsive pacemaker, as set forth in claim 1, wherein said means for computing a long-term running average of said sensor input signal comprises means for averaging said sensor input signal for at least thirty (30) of said first prescribed time periods.

4. The rate-responsive pacemaker, as set forth in claim 1, further comprising:
timing means for determining said second prescribed time period, said second prescribed time period corresponding to approximately 18 hours.

5. The rate-responsive pacemaker, as set forth in claim 1, wherein said sensor input signal includes a plurality of peak values when monitored over a third prescribed time period, and wherein said means for automatically determining the offset value that is added to said long-term average comprises means for defining the offset value to be an average of the peak values of said sensor input signal over the third prescribed time period.

6. The rate-responsive pacemaker, as set forth in claim 1, wherein said means for providing stimulation pulses comprises:
means for providing said stimulation pulses at a pacing rate also dependent upon a programmably selectable slope value of said sensor input signal.

7. An implantable, programmable rate-responsive pacemaker comprising:
a physiological sensor that includes means for sensing a physiological parameter and means for generating a sensor input signal as a function of a short-term average of the sensed physiological parameter for a first prescribed time period;
an averaging circuit coupled to receive said sensor input signal that includes means for determining a long-term running average of the sensor input signal over a second prescribed time period;
a threshold circuit, coupled to said averaging circuit, that includes means for determining when the sensor input signal exceeds said long-term running average of the sensor input signal plus a selectable offset value for determining a difference signal thereof as an output, said selectable offset value comprising a selected one of a plurality of fixed autothreshold offset values; and
a pulse generator, responsive to the threshold circuit, that includes means for generating stimulation pulses on demand at a pacing rate dependent upon said difference signal.

8. The rate-responsive pacemaker, as set forth in claim 7, wherein the physiological sensor comprises a piezoelectric crystal that senses physical activity.

9. The rate-responsive pacemaker, as set forth in claim 7, further comprising:
timing means for determining said first prescribed time period, said first prescribed time period corresponding to at least one pacing cycle.

10. The rate-responsive pacemaker, as set forth in claim 7, wherein said averaging circuit comprises:
means for computing a long-term average of the sensor input signal based on at least thirty (30) samples of the sensor input signal.

11. The rate-responsive pacemaker, as set forth in claim 7, further comprising:
timing means for determining said second prescribed time period, said second prescribed time period corresponding to approximately 18 hours.

12. The rate-responsive pacemaker, as set forth in claim 7, wherein said pulse generator comprises:
means for providing stimulation pulses on demand at a pacing rate also dependent upon a programmably selectable slope value of said sensor input signal.

13. A method of automatically setting a threshold value of a rate-responsive pacemaker, said rate-responsive pacemaker having a physiological sensor that senses a physiological parameter and generates a sensor input signal as a function thereof, said threshold value providing a reference value that the sensor input signal must exceed before such sensor input signal is considered as evidence of significant physiological activity to which the rate-responsive pacemaker should respond, said method comprising the steps of:
(a) processing the sensor input signal over a prescribed time period to provide a reference sensor input signal that is representative of the sensor input signal during said prescribed time period;
(b) programmably selecting one of a plurality of automatically determined offset values; and
(c) adding the offset value selected in step (b) to the reference sensor input signal determined in step (a) to obtain said threshold value.

14. The method, as set forth in claim 13, wherein step (a) comprises averaging the sensor input signal.

15. The method, as set forth in claim 14, further comprising the step of:
defining said prescribed time period as however long it takes to obtain at least thirty (30) readings of said sensor input signal.

16. The method, as set forth in claim 15, further comprising the step of:
defining said prescribed time period as at least 18 hours.

17. The method, as set forth in claim 13, wherein the reference sensor input signal includes a plurality of peak values over said prescribed time period, and wherein the automatically determined offset value is determined by averaging the peak values of the reference sensor input signal over said prescribed time period.

18. An implantable, programmable rate-responsive pacemaker comprising:
a physiological sensor that includes means for sensing a physiological parameter and means for generating a sensor input signal as a function of a short-term average of the sensed physiological parameter for a first prescribed time period, said sensor input signal having a plurality of peak values as a function of variations in such sensed physiological parameter;
an averaging circuit, coupled to receive said sensor input signal, that includes means for determining a long-term running average of the sensor input signal over a second prescribed time period;
a threshold circuit, coupled to said averaging circuit, that includes means for determining when the sensor input signal exceeds said long-term running average of the sensor input signal plus an offset value for determining a difference signal thereof as an output, said offset value comprising an average of the peak values of the sensor input signal over a third prescribed time period; and
a pulse generator, responsive to the threshold circuit, that includes means for generating stimulation pulses on demand at a pacing rate dependent upon said difference signal.

* * * * *